United States Patent [19]

Weinstein

[11] Patent Number: 5,107,038
[45] Date of Patent: Apr. 21, 1992

[54] PROCESS FOR THE PREPARATION OF CYCLOHEXANOL DERIVATIVES

[75] Inventor: Robert M. Weinstein, Geneva, Switzerland

[73] Assignee: Firmenich SA, Geneva, Switzerland

[21] Appl. No.: 602,040

[22] Filed: Oct. 22, 1990

[30] Foreign Application Priority Data

Nov. 13, 1989 [CH] Switzerland .............. 4072/89

[51] Int. Cl.⁵ .................................. C07C 35/08
[52] U.S. Cl. ............................ 568/834; 568/837
[58] Field of Search .............. 568/834, 830, 837

[56] References Cited

U.S. PATENT DOCUMENTS

| 2,927,127 | 3/1960 | Somerville et al. | 568/834 |
| 4,343,955 | 8/1982 | Oshima et al. | 568/834 |
| 4,508,918 | 4/1985 | Yasuhara et al. | 568/834 |

FOREIGN PATENT DOCUMENTS

| 2819159 | 11/1979 | Fed. Rep. of Germany . |
| 2273783 | 2/1976 | France . |
| 416606 | 1/1967 | Switzerland . |
| 1503723 | 3/1978 | United Kingdom . |

Primary Examiner—Alan Siegel
Assistant Examiner—Margaret Argo
Attorney, Agent, or Firm—Pennie & Edmonds

[57] ABSTRACT

A process for the preparation of 4-tert-butyl-cyclohexanol, comprising the hydrogenation of 4-tert-butyl-phenol or of 4-tert-butyl-cyclohexanone in the presence of a catalytic system composed of rhodium on a $Al_2O_3$, $SiO_2$, $TiO_2$, $SiO_2.Al_2O_3$ or charcoal support, in combination with $HBF_4$ or $BF_3.[Y]_n$ wherein Y designates a $R_2O$ group, R being a $C_1$ to $C_6$ lower alkyl radical, or a $CH_3CO_2H$, $H_3PO_4$ or $H_2O$ group and index n is equal to zero, 1 or 2.

11 Claims, No Drawings

PROCESS FOR THE PREPARATION OF CYCLOHEXANOL DERIVATIVES

BRIEF SUMMARY OF THE INVENTION

The present invention relates to a process for the preparation of 4-tert-butyl-cyclohexanol essentially in the form of its cis isomer, which process comprises the hydrogenation of 4-tert-butyl-phenol or of 4-tert-butyl-cyclohexanone in the presence of a catalytic system composed of rhodium on a $Al_2O_3$, $SiO_2$, $TiO_2$, $SiO_2.Al_2O_3$ or charcoal support, in combination with $HBF_4$ or $BF_3.[Y]_n$ wherein Y designates a $R_2O$ group, R being a $C_1$ to $C_6$ lower alkyl radical, or a $CH_3CO_2H$, $H_3PO_4$ or $H_2O$ group and index n is equal to zero, 1 or 2.

The invention further provides a catalytic system composed of rhodium on a $Al_2O_3$, $SiO_2$, $TiO_2$, $SiO_2.Al_2O_3$ or charcoal support, in combination with $HBF_4$ or $BF_3.[Y]_n$ wherein Y designates a $R_2O$ group, R being a $C_1$ to $C_6$ lower alkyl radical, or a $CH_3CO_2H$, $H_3PO_4$ or $H_2O$ group and index n is equal to zero, 1 or 2.

BACKGROUND OF THE INVENTION

The present invention relates to the perfume industry. More particularly, it concerns a new process for the preparation of 4-tert-butyl-cyclohexanol essentially in the form of its cis isomer. This compound is useful in the fragrance industry, particularly as an intermediate product for the preparation of esters, namely acetic ester.

Specifically, 4-tert-butyl-cyclohexyl acetate is a well-known perfuming ingredient, which is available on the market under several tradenames. It is generally commercialized in the form of an isomeric mixture wherein the cyclanic cis isomer is present in varied proportions, more often in an amount between 30 and 65% by weight. Now, it has been established that there is a fundamental difference between the olfactive quality of this cis isomer and that of the corresponding trans isomer, the first of these compounds being preferred [see Arctander, Perfume and Flavor Chemicals, Montclair, N.J. (1969), sects. 440 and 441]. For this reason, a great number of research groups have directed their efforts towards the preparation of said ester in its preferred isomeric form. Nevertheless, the problem of the availability of a product rich in the cis isomer remains of actuality. As a matter of fact, while some of the numerous syntheses disclosed in the prior art provide isomeric mixtures with an adequate content in cis isomer, this is only achieved at the cost of expensive technical solutions which render their industrial exploitation not very profitable.

U.S. Pat. No. 2,927,127, granted on Mar. 1, 1960, describes a process for the preparation of a cis/trans mixture of 4-tert-butyl-cyclohexyl acetate having a content in cis isomer as high as 87.5%, which process consists in the catalytic hydrogenation of p-tert-butyl-phenol in the presence of Rh on an active charcoal support and in the acetylation, by means of acetic anhydride, of the product thus obtained. The hydrogenation step is carried out at a high pressure, of the order of $7 \times 10^6$ Pa.

Likewise, in Chemical Abstracts, vol. 80, sec. 14700s, there is disclosed a process for reducing p-tert-butyl-phenol by means of a catalytic hydrogenation with Rh on active charcoal or with ruthenium dioxide, at a pressure of $10 \times 10^6$ Pa. The reported content in cis isomer was 64.1%.

U.S. Pat. No. 4,343,955 teaches a process for the preparation of p-tert-butyl-cyclohexanol by catalytic hydrogenation in the presence of ruthenium on alumina, at a pressure of $4 \times 10^6$ Pa and a temperature of 100° C. In this case, the content of the resulting product in cis isomer was 74.8%.

Finally, European Patent No. 141,054 describes a two-step process comprising the reduction of p-tert-butyl-phenol by means of palladium on alumina, at 120°-180° C. and a pressure above $20 \times 10^6$ Pa, followed by the hydrogenation of the resulting product in the presence of ruthenium on same alumina support, at a temperature of 70°-200° C. and under the same pressure conditions. The cis isomer was present in the obtained mixture in an amount of the order of 46%.

As described, the prior art processes resorted to methods requesting drastic reaction conditions, thus creating technical problems of a particular nature when such methods are applied at an industrial scale. On the other hand, it is well-known that amongst the questions to be considered when applying industrially a process which uses heterogeneous catalysis, lies that of the feasibility of recycling the catalyst, as well as the concern for its lifetime and reactivation. All these factors enter into account when determining the worth of a process from an economical point of view and are, as a result, critical factors when said process is put into industrial application.

It has now been discovered that, henceforth, it is possible to obtain isomeric mixtures of 4-tert-butyl-cyclohexanol which are rich in the cis isomer, through a process that, in addition, presents clear advantages over the prior art methods in what concerns the recycling of the catalyst. Although this process comprises the catalytic hydrogenation of 4-tert-butyl-phenol or of 4-tert-butyl-cyclohexanone in the presence of a rhodium-based catalyst, it allows nevertheless the application of mild reaction conditions. It has in fact been observed that the use of a catalyst composed of rhodium previously deposited on an alumina support in the presence of a co-catalyst such as boron trifluoride, not only made it possible to obtain an excellent stereoselectivity, but also provided a catalytic system the activity of which remained constant and adequate over a high number of operations, thus rendering the process more cost-effective. While the use of fluorinated catalysts of the type $BF_3.Al_2O_3$ has been described in the context of alkylation reactions involving aromatic systems and $KF.Al_2O_3$ has been reported as a catalyst in simple addition-type reactions [see J. Chem. Soc. 1986, 1133-39], there are few reports of the use of such catalysts in hydrogenation reactions and, to the best of our knowledge, their use in the stereoselective hydrogenation of cyclohexanones or phenols, to yield cyclohexanols, has never been suggested. As a co-catalyst, $BF_3$ may be employed as such or in the form of one of its complexes.

THE INVENTION

The object of the present invention is, therefore, to provide a process for the preparation of 4-tert-butyl-cyclohexanol essentially in the form of its cis isomer, which process comprises the hydrogenation of 4-tert-butyl-phenol or of 4-tert-butyl-cyclohexanone in the presence of a catalytic system composed of rhodium on a $Al_2O_3$, $SiO_2$, $TiO_2$, $SiO_2.Al_2O_3$ or charcoal support, in combination with $HBF_4$ or $BF_3.[Y]_n$ wherein Y designates a $R_2O$ group, R being a $C_1$ to $C_6$ lower alkyl radical. or a $CH_3CO_2H$, $H_3PO_4$ or $H_2O$ group and index n is equal to zero, 1 or 2.

The reaction which characterizes this process is schematically illustrated as follows:

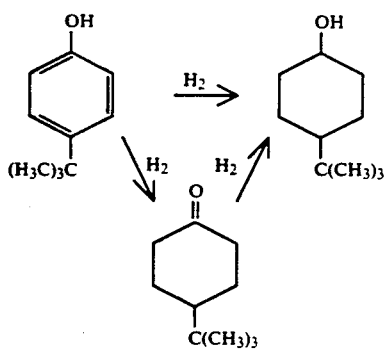

Although the hydrogenation reaction may be carried out at atmospheric pressure, it was observed that the best yields, as well as the most favorable isomeric distribution, were obtained when pressures of the order of $3 \times 10^5$ Pa to around $2 \times 10^6$ Pa were applied.

The temperature was not a critical factor. As a result of the use of the new catalytic system, the reaction can be carried out at temperatures close to room temperature. According to a preferred embodiment of the process of the invention, good final product yields are obtained when temperatures of the order of 25° to 200° C. are used, and 40°-130° C. are typical temperature values, adapted to most practical cases.

The conversion rates observed were excellent and reached 100% in many cases, while the good steroselectivity of the catalytic system used finds expression in the production of isomeric mixtures of 4-tert-butyl-cyclohexanol whose content in the preferred cis isomer can reach around 90% by weight.

Under the reaction conditions defined above, the reaction times are of the order of a few hours. In many cases, 2 to 5 hours are enough to achieve almost complete conversion of the starting phenol or cyclohexanone.

Without wanting to speculate on the real structure of the catalytic system employed, it is apparent that the use of a "co-catalyst" such as $BF_3$ resulted in a modification of the nature of the surface of the alumina support, thus imparting thereto a stoichiometry which can be better defined as $[Al_2O_3]_{0.8} \cdot [AlF_3]_{0.2}$. Typically, catalysts composed of 5% by weight of rhodium on $Al_2O_3$ were used. These are common concentration values for commercially available grades of $Rh/Al_2O_3$.

One of the critical parameters in ensuring that the reaction is carried out in good conditions is the ratio of relative proportions of $BF_3$ and rhodium. I have been able to establish that this ratio, defined in molar quantities, could be comprised between about 0.5 and 15; however, I observed that an increase in the proportion of $BF_3$ led to the formation of undesirable side-products. Finally, the amount of catalyst, defined in terms of the molar quantity of rhodium versus the molar quantity of phenols or cyclohexanols, could be of the order of 0.1-0.5%.

The hydrogenation takes place in an organic solvent inert under the reaction conditions and, to this end, it is convenient to use an ether, for example tetrahydrofuran, or an aliphatic or cycloaliphatic hydrocarbon such as, for example, cyclohexane.

The specific and preferred catalyst used in the process according to the invention, which is also an object of the latter, can be conveniently prepared by impregnation of $Rh/Al_2O_3$. Thus, a mixture of $BF_3.O(C_2H_5)_2$, or trifluoroboroetherate, with $Rh/Al_2O_3$ in ethyl acetate, was kept at around 45° C. under argon for 75 min, and the solid product was subsequently isolated and dried. Before its use, the catalyst thus obtained is maintained under inert gas atmosphere. It was observed that, when treated in this manner, the catalyst maintained its specific activity for 7 days at least. Although the catalytic system thus prepared is perfectly adapted to all practical use of concern, other efficient systems can be obtained by simply adding the co-catalyst to $Rh/Al_2O_3$ or Rh/C. Thus, tetrafluoroboric acid can be directly added to the reaction mixture upon hydrogenation in the presence of rhodium on alumina or on charcoal. Such a system shows a stereospecificity which is fully comparable to that of the above-described previously impregnated catalyst.

The invention will now be described in greater detail by way of the following examples, wherein the temperatures are indicated in degrees centigrade and the abbreviations have the usual meaning in the art.

EXAMPLE 1

Preparation of the Catalyst

General method by impregnation

A. 10 g of 5% (parts by weight) rhodium on a commercial alumina support equivalent to 0.50 g or 4.86 mmole, 0.920 ml of $BF_3.O(C_2H_5)_2$ [distilled before use; 7.48 mmole] and 60 ml of ethyl acetate were charged into a 100 ml flask under nitrogen. After mixing, the flask was stirred by means of a rotating evaporator at 45° and around $9.3 \times 10^4$ Pa for 75 min, then the mixture was concentrated until dry. A solid product was thus obtained which was kept under argon until used.

B. 3 g of 5% (parts by weight) rhodium on a $TiO_2$ support, 0.276 ml of $BF_3.O(C_2H_5)_2$ [distilled before use] and 18 ml of ethyl acetate were introduced into a reactor under argon. The resulting mixture was kept under mild stirring for about 1 h 15 at 45° by means of a rotating evaporator. It was then concentrated to dryness. The catalyst obtained in this manner was kept under argon until used.

Preparation of 4-Tert-Butyl-Cyclohexanol

A mixture consisting of 50 g (0.33 mole) of 4-tert-butyl-phenol, 1.35 g of the catalyst prepared as described above under example 1A and 100 g of cyclohexane was introduced in an autoclave under nitrogen and then hydrogen was introduced until a stable pressure around $16 \times 10^5$ Pa had been established. The reaction mixture was then heated to about 98° and the reaction was followed by gas chromatography.

After 135 min, the reaction was interrupted by cooling to around 45° and the autoclave was purged with a nitrogen flow. After filtering, the catalyst was recovered under a flow of argon, washed with cyclohexane and recycled for the following hydrogenation operations.

4-tert-Butyl-cyclohexanol was obtained by distillation of the clear filtrate in 98% yield. The isomeric content was 81.9% of the cis isomer and 15.9% of the trans isomer.

EXAMPLES 2-5

A mixture composed of 86.72 g of 4-tert-butyl-phenol (0.578 mole), 2.31 g of 5% by weight rhodium on alumina [equivalent to 1.12 mmole of rhodium], 2.50 ml of tetrafluoroboric acid in a 31% solution [equivalent to 11.4 mmole of $HBF_4$] and 200 ml of tetrahydrofuran were introduced in an autoclave equipped with a stirrer under nitrogen, then hydrogen was introduced until the pressure settled down at around $5 \times 10^5$ Pa.

The mixture was kept under vigorous stirring for about 24 hours at room temperature.

After filtering and the usual concentration work-up, 4-tert-butyl-cyclohexanol was obtained in almost quantitative yield. The cis/trans isomeric ratio was 84.1/15.9.

Other experiments were carried out according to the general procedure described above and replacing $HBF_4$ by the complexes indicated hereinafter. Facing the catalytic complex used is indicated the cis/trans isomeric ratio of the obtained 4-tert-butyl-cyclohexanol.

| Example | Catalyst | Isomeric ratio cis/trans |
|---|---|---|
| 3 | $Rh/Al_2O_3$ + $BF_3.2CH_3CO_2H$ | 81/19 |
| 4 | $Rh/Al_2O_3$ + $BF_3.H_3PO_4$ | 85/13 |
| 5 | $Rh/Al_2O_3$ + $BF_3.2H_2O$ | 81/18 |

EXAMPLE 6

Preparation of 4-tert-butyl-cyclohexanol

A mixture composed of 100 g (0.649 mole) of 4-tert-butyl-cyclohexanone, 1.35 g of the catalyst prepared as indicated in Example 1 and 150 g of cyclohexane were put into an autoclave under nitrogen and then hydrogen was introduced until the pressure settled at about $10^6$ Pa. The mixture was then heated to 70° and the reaction was followed by gas chromatography. The reaction was stopped by cooling and the autoclave was flushed with nitrogen. After filtering, the catalyst was recovered under argon flow, washed with cyclohexane and recycled for the following hydrogenation operations. The clear filtrate was evaporated to give a residue that, once distilled, provided 95.15 g of an isomeric mixture containing 87.7% of cis isomer.

EXAMPLE 7

Preparation of 4-tert-butyl-cyclohexanol

By treatment of 50 g of 4-tert-butyl-phenol in the presence of 1.35 g of the catalyst prepared according to the process described above in Example 1B and carrying out the reaction as indicated in Example 1, a mixture of 4-tert-butyl-cyclohexanol having a content in cis isomer of 82.9% was obtained.

EXAMPLE 8

Catalyst recycling (lifetime) experiments 2 kg (13,33 mole) of 4-tert-butyl-phenol, 2 kg of cyclohexane and 28 g of the catalyst prepared as indicated in Example 1A were placed in an autoclave which had been purged 3 times with nitrogen. Hydrogen was then introduced until the pressure settled down at $16 \times 10^5$ Pa. The reaction was followed by GC and stopped when the conversion indicated a content in intermediate 4-tert-butyl-cyclohexanone of 1% or lower. The reaction mixture was then treated as described in the preceding examples. The catalyst isolated by filtration was used in successive reactions as indicated in the following Table.

| Reaction n° | Reaction time (hours) | % cis-Alcohol | % trans-Alcohol |
|---|---|---|---|
| 1 | 1.8 | 84.7 | 14.5 |
| 2 | 2.0 | 84.0 | 15.5 |
| 3 | 2.3 | 83.8 | 15.4 |
| 4 | 3.0 | 83.8 | 15.6 |
| 5 | 3.0 | 83.1 | 15.8 |
| 6 | 2.5 | 83.2 | 15.8 |
| 7 | 2.8 | 83.9 | 15.3 |
| 8 | 3.0 | 82.1 | 15.0 |
| Average | | 83.6 ± .8 | 15.4 ± .4 |

What I claim is:

1. A process for the preparation of 4-tert-butyl-cyclohexanol, predominantly in the form of its cis isomer, which comprises hydrogenating 4-tert-butyl-cyclohexanone in the presence of a catalytic system comprising rhodium on a suitable support, in combination with $HBF_4$ or $BF_3.[Y]_n$ wherein Y designates a $R_2O$ group, R being a $C_1$ to $C_6$ lower alkyl radical, or a $CH_3CO_2H, H_3PO_4$ or $H_2O$ group and n is equal to zero, 1 or 2, at an effective temperature and pressure to prepare 4-tert-butyl-cyclohexanol.

2. The process of claim 1 which further comprises selecting the support to be one of $Al_2O_3$, $SiO_2$, $TiO_2$, $SiO_2.Al_2O_3$ or charcoal.

3. The process of claim 1, wherein the catalytic system is formed of $Rh/Al_2O_3.BF_3$.

4. The process of claim 1, wherein the ratio between the respective proportions of $BF_3$ and rhodium, expressed in molar quantities, is about 0.5 to 15.

5. The process of claim 4 wherein the $BF_3$: rhodium molar ratio is from 0.5 to 5.

6. The process of claim 1, wherein the hydrogenation is carried out at a pressure of between $3 \times 10^5$ and $2 \times 10^6$ Pa and a temperature between 25° and 200° C.

7. The process of claim 6, wherein a temperature from 40° to 130° C. is used.

8. The process of claim 1, wherein the molar quantity of rhodium, relative to the molar quantity of starting 4-tert-butyl-cyclohexanone ranges from 0.01 to 0.5%.

9. The process of claim 1, wherein the hydrogenation is carried out in an organic solvent which is inert under the reaction conditions.

10. The process of claim 8, wherein the hydrogenation is carried out in cyclohexane.

11. The process of claim 1 wherein the cis isomer is present in an amount of at least 81.9%.

* * * * *